United States Patent [19]

Callejas et al.

[11] 4,251,674
[45] Feb. 17, 1981

[54] METHOD AND APPARATUS FOR IMPROVING THE SELECTIVITY OF A PROCESS FOR HYDROGENATING ACETYLENE TO ETHYLENE

[75] Inventors: Ricardo J. Callejas, Maracaibo, Venezuela; John R. Mitchell, Sweeny, Tex.

[73] Assignee: Phillips Petroleum Company, Bartlesville, Okla.

[21] Appl. No.: 87,272

[22] Filed: Oct. 22, 1979

[51] Int. Cl.³ .......................... C07C 5/09; C07C 11/04
[52] U.S. Cl. ............................... 585/272; 23/230 A; 208/DIG. 1; 585/259; 585/263; 585/271; 422/62
[58] Field of Search ............... 585/271, 324, 259, 261, 585/263-264, 272, 841; 422/62; 23/230 A

[56] References Cited

U.S. PATENT DOCUMENTS

| | | | |
|---|---|---|---|
| 2,802,889 | 8/1957 | Frevel et al. | 585/262 |
| 3,113,980 | 12/1963 | Robinson et al. | 585/260 |
| 3,187,064 | 6/1965 | Wang et al. | 585/259 |
| 3,471,582 | 10/1969 | Luper | 585/259 |
| 3,634,536 | 1/1972 | Frevel et al. | 585/261 |
| 3,656,911 | 4/1972 | Hobbs | 422/62 |
| 3,662,015 | 5/1972 | Komatsu et al. | 585/274 |
| 3,674,886 | 7/1972 | Komatsu et al. | 585/277 |
| 3,839,483 | 10/1974 | Carr et al. | 585/259 |
| 4,020,119 | 4/1977 | Johnson et al. | 585/259 |
| 4,166,830 | 9/1979 | Guth et al. | 585/259 X |

Primary Examiner—Delbert E. Gantz
Assistant Examiner—G. E. Schmitkons

[57] ABSTRACT

In an ethylene manufacturing process in which the effluent from the cracking furnaces is provided to an acetylene reactor to therein selectively hydrogenate acetylene to ethylene, method and apparatus is provided whereby methanol is injected into the cracking furnace to produce carbon monoxide in sufficient quantities to substantially optimize the selectivity of the conversion of acetylene to ethylene in the acetylene reactors. The concentration of the carbon monoxide in the effluent flowing from the cracking furnace is utilized to manipulate the flow of methanol to the cracking furnace so as to maintain a desired concentration of carbon monoxide in the effluent flowing from the cracking furnace.

9 Claims, 1 Drawing Figure

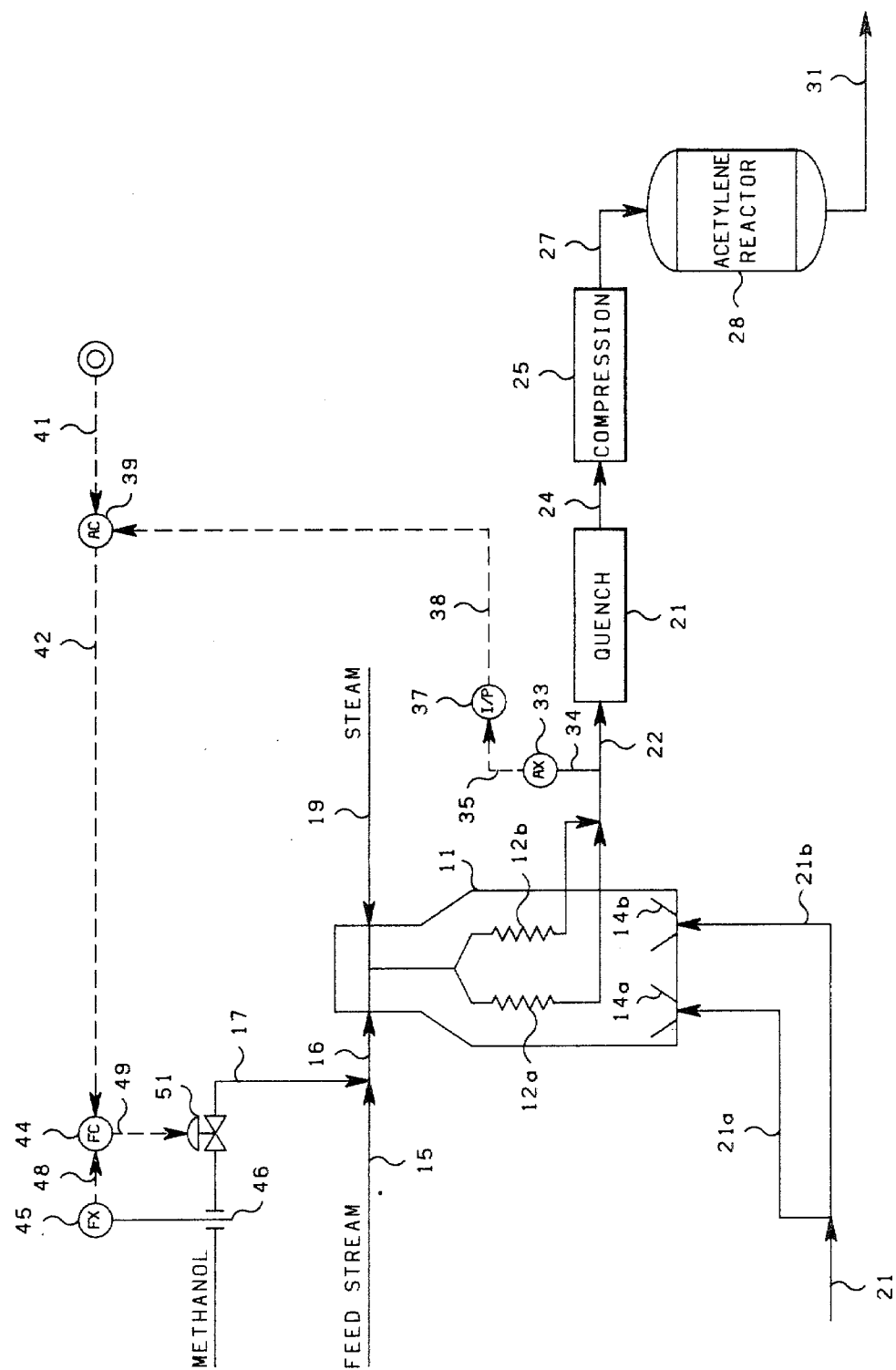

METHOD AND APPARATUS FOR IMPROVING THE SELECTIVITY OF A PROCESS FOR HYDROGENATING ACETYLENE TO ETHYLENE

This invention relates to method and apparatus for improving the selectivity of a process for hydrogenating acetylene to ethylene in an acetylene reactor. In one aspect this invention relates to method and apparatus for maintaining the carbon monoxide concentration in a mixed hydrocarbon stream at a level which will substantially optimize the selectivity of the hydrogenation of acetylene to ethylene in an acetylene reactor.

Ethylene is commonly produced by the thermal cracking of hydrocarbon feedstocks. Generally, some acetylene is also produced and this acetylene must be removed for many applications. The removal of the acetylene is generally accomplished by the selective catalytic hydrogenation of the acetylene.

Catalysts such as the catalyst disclosed in U.S. Pat. No. 4,020,119 are generally used in the selective catalytic hydrogenation of the acetylene. U.S. Pat. No. 4,020,119 discloses that the selectivity of a hydrogenation process can be improved by incorporating carbon monoxide in the feedstock to the hydrogenation process. Generally, some carbon monoxide is formed in the cracking furnace. However, the concentration of the carbon monoxide will vary depending upon the feed to the cracking furnace and the cracking conditions. Further, the presence of sulfur in the feed to the cracking furnace may seriously inhibit the formation of carbon monoxide. Thus, the concentration of carbon monoxide in the effluent flowing from the cracking furnace may vary over a wide range depending upon the makeup of the feedstock flowing to the cracking furnace, the cracking conditions and the concentration of sulfur in the feedstock flowing to the cracking furnace. This possible wide variance in the concentration of carbon monoxide in the feed flowing to the acetylene reactor causes substantial difficulty in controlling the acetylene reactor and optimizing the selectivity of the hydrogenation reaction. It is thus an object of this invention to provide method and apparatus for maintaining the carbon monoxide concentration in the effluent flowing from the cracking furance at a substantially constant level which will substantially optimize the selectivity of the hydrogenation of acetylene to ethylene in an acetylene reactor.

In accordance with the present invention, method and apparatus is provided whereby methanol is injected into the feed flowing to the cracking furnace. Under the conditions of the cracking furnace in an ethylene manufacturing process, it is well known that methanol is converted to carbon monoxide and hydrogen. The concentration of carbon monoxide and the effluent flowing from the cracking furnace is measured. This actual concentration is compared to the desired concentration and a control signal which is responsive to the difference between the actual and the desired concentrations of the carbon monoxide is utilized to manipulate the flow rate of the methanol flowing to the cracking furnace so as to maintain the concentration of carbon monoxide in the effluent flowing from the cracking furnace substantially constant at the desired level. In this manner, variations in the concentration of carbon monoxide in the effluent flowing from the cracking furnace are substantially reduced which prevents process upsets in the acetylene reactor. Further, the concentration of carbon monoxide in the effluent flowing from the cracking furnace is maintained at a desired level which will substantially optimize the selectivity of the hydrogenation of acetylene to ethylene in an acetylene reactor.

Other objects and advantages of the invention will be apparent from the foregoing brief description of the invention and the claims are well as the detailed description of the drawing in which:

The FIGURE is a diagrammatic view of a cracking furnace and acetylene reactor for an ethylene manufacturing process together with a control system for maintaining the concentration of carbon monoxide in the effluent flowing from the cracking furnace at a substantially constant, desired level.

The invention is illustrated and described in terms of a specific ethylene manufacturing process. However, the invention is applicable to other process configurations for an ethylene manufacturing process in which other processes such as deethanizing may be carried out prior to the acetylene hydrogenation step. Further, for the sake of simplicity, the invention is illustrated and described in terms of a single cracking furnace and a single acetylene reactor. However, the invention is applicable to multiple cracking furnaces and multiple acetylene reactors or acetylene reactors employing two or more reaction stages.

Although the invention is illustrated and described in terms of a specific control system, the invention is also applicable to different control system configurations which accomplish the purpose of the invention. Lines designated as signal lines in the drawings are pneumatic in this preferred embodiment except for the output from the analyzer which is electrical. However, the invention is also applicable to electrical, mechanical, hydraulic or other signal means for transmitting information. In almost all control systems some combination of these types of signals will be used. However, use of any type of signal transmission, compatible with the process and equipment in use is within the scope of the invention.

The controllers shown may utilize the various modes of control such as proportional, proportional-integral, proportional-derivative, or proportional-integral-derivative. In this preferred embodiment, proportional-integral controllers are utilized but any controller capable of accepting two input signals and producing a scaled output signal, representative of a comparison of the two input signals, is within the scope of the invention. The operation of proportional-integral controllers is well known in the art. The output control signal of a proportional-integral controller may be represented as $$S = K_1 E + K_2 \int E\, dt$$

where
 S = output control signals;
 E = difference between two input signals; and
 $K_1$ and $K_2$ = constants.

The scaling of an input signal by a controller is well known in control systems art. Essentially, the output of a controller may be scaled to represent any desired factor or variable. An example of this is where a desired concentration and an actual concentration is compared by a controller. The output could be a signal representative of a desired change in the flow rate of some gas necessary to make the desired and actual concentration equal. On the other hand, the same output signal could be scaled to represent a percentage or could be scaled to represent a temperature change required to make the desired and actual concentration equal. If the controller output can range from 3 to 15 lbs., which is typical, then the output signal could be scaled so that an output signal having a voltage level of 9 lbs. corresponds to 50 percent, some specified flow rate, or some specified temperature.

Referring now to the drawing, a conventional cracking furnace 11 is illustrated having two cracking tubes 12a and 12b. Heat is supplied to the two cracking tubes 12a and 12b by means of burners 14a and 14b, respectively. The cracking furnace 11 is illustrated as having only two burners and two cracking tubes for the sake of convenience. Ordinarily, a cracking furnace used in an ethylene manufacturing process will have a larger number of cracking tubes and burners. Also a plurality of cracking furnaces will commonly be utilized.

A hydrocarbon such as ethane and/or propane is provided as a feed gas to the cracking furnace 11 through the combination of conduit means 15 and 16. Methanol is provided to the cracking furnace 11 through the combination of conduit means 17 and 16. Steam is provided to the cracking furnace 11 through conduit means 19. The feed stream, methanol and steam are combined within the cracking furnace 11 and flow through the cracking tubes 12a and 12b. After passing through the cracking tubes 12a and 12b in which the feed gas is converted to ethylene, propylene and other gases, the gaseous mixture is combined and flows to the quench operation 21 through conduit means 22. The methanol provided to the cracking furnace will be converted to carbon monoxide and hydrogen and will also be provided with the effluent flowing from the cracking furnace 11 through conduit means 22 to the quench operation 21.

Fuel is supplied to the cracking furnace 11 through conduit means 21. Specifically, fuel is supplied to the burner 14a through conduit means 21a which is operably connected to conduit means 21. Fuel is supplied to the burner 14b through conduit means 21b which is also operably connected to conduit means 21.

The effluent flowing from the cracking furnace 11 will be quenched in the quench operation 21 and will be provided from the quench operation 21 through conduit means 24 to the compression system 25. The effluent is compressed in the compression system 25 and is provided through conduit means 27 to the acetylene reactor 28. As has been previously stated, the acetylene reactor 28 employs a catalyst such as that disclosed in U.S. Pat. No. 4,020,119 to selectively hydrogenate the acetylene in the effluent flowing through conduit means 27 to ethylene. The effluent flowing from the acetylene reactor through conduit means 31 will thus have a greatly decreased concentration of acetylene. The effluent flowing through conduit means 31 is provided to other parts of the ethylene manufacturing processes such as the deethanizer or demethanizer.

It is again noted that the specific process steps set forth in the FIGURE are not critical to the present invention. Many ethylene manufacturing processes use different process steps. However, it is essential that a process step such as demethanization which would remove a large percentage of the carbon monoxide not be employed prior to the acetylene hydrogenation.

Analyzer transducer 33, which is preferably a chromatographic analyzer, is operably connected to the conduit means 22 through conduit means 34. Analyzer transducer 33 provides an output signal 35 which is representative of the actual concentration of carbon monoxide in the effluent flowing through conduit means 22. This carbon monoxide will be supplied by the cracking of the methanol and will also in part be supplied by the cracking of the feed stream. Signal 35 is provided as an input to the current-to-pressure (I/P) transducer 37 from the analyzer transducer 33. Signal 35 is converted from electrical form to pneumatic form by the I/P converter 37 and is provided as signal 38 to the analyzer controller 39. The analyzer controller 39 is also provided with a set point signal 41 which is representative of the desired concentration of carbon monoxide in the effluent flowing through conduit means 22. In response to signals 38 and 41, the analyzer controller 39 provides an output signal 42 which is responsive to the difference between signals 38 and 41. Signal 42 is scaled in the manner previously described so as to be representative of the flow rate of the methanol flowing through conduit means 17 required to maintain the actual concentration of the carbon monoxide in the effluent flowing through conduit means 22 equal to the desired concentration. Signal 42 is provided from the analyzer controller 39 as a set point signal to the flow controller 44.

Flow transducer 45 in combination with flow sensor 46, which is operably located in conduit means 17, provides an output signal 48 which is representative of the flow rate of the methanol flowing through conduit means 17. Signal 48 is provided from the flow transducer 45 as a second input to the flow controller 44. In response to signals 42 and 48, the flow controller 44 provides an output signal 49 which is responsive to the difference between signals 42 and 48. Signal 49 is provided from the flow controller 44 as a control signal to the pneumatic control valve 51 which is operably located in conduit means 17. Signal 49 is scaled so as to be representative of the opening of the pneumatic control valve 51 which is required to maintain the actual flow rate of the methanol flowing through conduit means 17 equal to the flow rate required to maintain the carbon monoxide concentration in the effluent flowing through conduit means 22 equal to the desired concentration.

Any suitable carbon monoxide concentration for substantially optimizing the selectivity of the hydrogenation of the acetylene to ethylene in the acetylene reactor 28 can be maintained in the effluent flowing through conduit means 22. Carbon monoxide concentrations in the amounts of about 50 to about 100,000 parts per million, preferably from about 500 to about 5,000 parts per million of the effluent flowing through conduit means 22 have been found to be effective.

The present invention provides a control system whereby process upsets in the acetylene reactor due to variations in carbon monoxide concentration in the effluent flowing through conduit means 27 to the acetylene reactor 28 are minimized by maintaining the concentration of carbon monoxide substantially constant. The control system also provides a method and apparatus whereby the flow rate of methanol is manipulated to maintain the carbon monoxide concentration in the effluent flowing through conduit means 27 to the acetylene reactor 28 at a level which will substantially optimize the hydrogenation of the acetylene to ethylene.

The invention has been described in terms of a preferred embodiment as illustrated in the FIGURE. Specific components which can be used in the practice of the invention as illustrated in the FIGURE are as follows:

Analyzer transducer 33

Optichrom 102 Chromatograph
Applied Automation

I/P transducer 37
Current-to pressure Transducer Model 7716
Moore Products Co.

Analyzer controller 39
Taylor Series 127R and Flow Controller 44
Taylor Instruments Other components such as the flow sensor 46, flow transducer 45 and pneumatic control valve 51 are each well known, commercially available control components such as are illustrated and described at length in Perry's Chemical Engineers Handbook, 4th Edition, Chapter 22, McGraw-Hill.

While the invention has been described in terms of the presently preferred embodiment, reasonable variations and modifications are possible by those skilled in the art, within the scope of the described invention and the appended claims.

That which is claimed is:

1. Apparatus comprising:
    a cracking furnace means;
    means for supplying a feed stream to said cracking furnace means;
    means for supplying methanol to said cracking furnace means;
    means for supplying a fuel to said cracking furnace means, the combustion of said fuel supplying heat to said cracking furnace means;
    an acetylene reactor means;
    means for removing a gaseous mixture, containing the cracked components of said feed stream and containing carbon monoxide, from said cracking furnace means and for supplying said gaseous mixture to said acetylene reactor means;
    means for establishing a first signal representative of the concentration of carbon monoxide in said gaseous mixture;
    means for establishing a second signal representative of the desired concentration of carbon monoxide in said gaseous mixture;
    means for comparing said first signal and said second signal and for establishing a third signal responsive to the difference between said first signal and said second signal; and
    means for manipulating the flow rate of said methanol to said cracking furnace means in response to said third signal to thereby maintain the actual concentration of said carbon monoxide in said gaseous mixture substantially equal to the desired concentration for said carbon monoxide in said gaseous mixture.

2. Apparatus in accordance with claim 1 wherein said means for manipulating the flow rate of methanol to said cracking furnace means in response to said third signal comprises:
    means for establishing a fourth signal representative of the actual flow rate of said methanol to said cracking furnace means;
    means for comparing said third signal and said fourth signal and for establishing a fifth signal responsive to the difference between said third signal and said forth signal; and
    means for manipulating the flow rate of said methanol to said cracking furnace means in response to said fifth signal.

3. Apparatus in accordance with claim 2 wherein said means for establishing said first signal comprises a chromatographic analyzer.

4. Apparatus in accordance with claim 3 wherein said means for comparing said first signal and said second signal is a proportional-integral controller and said means for comparing said third signal and said fourth signal is a proportional-integral controller.

5. Apparatus in accordance with claim 4 wherein said means for establishing said fourth signal is a flow transducer and said means for manipulating the flow rate of methanol to said cracking furnace means in response to said fifth signal is a pneumatic control valve means.

6. Apparatus in accordance with claim 5 wherein the desired concentration of said carbon monoxide in said gaseous mixture is in the range of about 500 to about 5000 parts per million of said gaseous mixture.

7. A method for maintaining a desired concentration of carbon monoxide in the gaseous mixture flowing from a cracking furnace to an acetylene reactor comprising the steps of:
    supplying a feed stream to said cracking furnace;
    supplying methanol to said cracking furnace;
    supplying a fuel to said cracking furnace, the combustion of said fuel supplying heat to said cracking furnace;
    removing said gaseous mixture, containing the cracked components of said feed stream and containing carbon monoxide, from said cracking furnace and supplying said gaseous mixture to said acetylene reactor;
    establishing a first signal representative of the concentration of carbon monoxide in said gaseous mixture;
    establishing a second signal representative of the desired concentration of carbon monoxide in said gaseous mixture;
    comparing said first signal and said second signal and establishing a third signal responsive to the difference between said first signal and said second signal; and
    manipulating the flow rate of said methanol to said cracking furnace in response to said third signal to thereby maintain the actual concentration of said carbon monoxide in said gaseous mixture substantially equal to the desired concentration for said carbon monoxide in said gaseous mixture.

8. A method in accordance with claim 7 wherein said step of manipulating the flow rate of methanol to said cracking furnace in response to said third signal comprises:
    establishing a fourth signal representative of the actual flow rate of said methanol to said cracking furnace;
    comparing said third signal and said fourth signal and establishing a fifth signal responsive to the difference between said third signal and said fourth signal; and
    manipulating the flow rate of said methanol to said cracking furnace in response to said fifth signal.

9. A method in accordance with claim 8 wherein the desired concentration of said carbon monoxide in said gaseous mixture is in the range of about 500 to about 5000 parts per million of said gaseous mixture.

* * * * *